United States Patent [19]
Chuiton et al.

[11] 4,265,248
[45] May 5, 1981

[54] DIFFERENTIAL OLFACTOMETER

[75] Inventors: René Chuiton, Clamart; Patrick MacLeod, Chatenay-Malabry, both of France

[73] Assignee: Commissariat A L'Energie Atomique, Paris, France

[21] Appl. No.: 969,257

[22] Filed: Dec. 13, 1978

[30] Foreign Application Priority Data

Jan. 10, 1978 [FR] France .............................. 78 00509

[51] Int. Cl.³ .............................................. A61B 5/00
[52] U.S. Cl. ..................................... 128/630; 128/747
[58] Field of Search ............... 128/630, 747, 716, 198, 128/200, 206, 207

[56] References Cited

U.S. PATENT DOCUMENTS

| 3,885,550 | 5/1975 | MacLeod | 128/630 |
| 4,106,493 | 8/1978 | Procter et al. | 128/747 X |
| 4,106,496 | 8/1978 | Procter et al. | 128/747 X |

FOREIGN PATENT DOCUMENTS

| 387706 | 9/1973 | U.S.S.R. | 128/630 |
| 520019 | 3/1976 | U.S.S.R. | 128/630 |

Primary Examiner—Kyle L. Howell
Attorney, Agent, or Firm—Lane, Aitken, Ziems, Kice & Kananen

[57] ABSTRACT

Differential olfactometer comprising two atomizers located on either side of a nasal support and respectively associated with a circuit for supplying olfactory stimuli, a retractable antidiffusion device which hides the atomizers during the intervals between nasal stimulation periods and a breathing detection device associated with an electronic control unit for controlling the hiding of the atomizers, wherein the supply circuit for the atomizers comprises means for permanently supplying the latter.

15 Claims, 6 Drawing Figures

DIFFERENTIAL OLFACTOMETER

BACKGROUND OF THE INVENTION

The present invention relates to a differential olfactometer. It relates to a physiological zero detector for measuring the intensities of odours of different olfactory stimuli.

It is known that the function of olfactometry is to supply an olfactory stimulus which is well defined as regards chemical composition and concentration. It uses devices able to dilute one or more odorous gases in an odourless gas, such as air or nitrogen.

Olfactometry fulfils two different requirements: the measurement of the olfactory threshold (liminal olfactometry) and the measurement of the intensity of odours (supraliminal olfactometry).

Liminal olfactometry is simple. It is in fact easy to measure a threshold. The experimental method consists of investigating the smallest concentration which the person is able to perceive with a 50% probability.

Supraliminal olfactometry is less simple. Two methods can be used:

one method consists of subjectively estimating the intensity, expressed by a figure between 0 and a maximum;

the other method consists of establishing the equalization between the experimental stimulus and a standard stimulus appropriately chosen within an intensity range, equalization taking place by successive approximations.

Another problem which is difficult to solve in olfactometry is that of dilution and the method of presenting the stimulus. The dilution can be static or dynamic, whilst the presentation of the stimulus can be active (by inhaling or smelling) or passive (by injecting into the nasal cavities of the person concerned).

Static dilution is obtained by introducing a known quantity of odorous substances into a known volume of odourless gas contained in an inert enclosure. Dynamic dilution is obtained by mixing a small odorous gaseous current with a large odourless gaseous current. By increasing the number of dilution stages a random concentration can be obtained in this way. The best results are obtained by using dynamic olfactometers with active presentation of the stimulus. In the case of supraliminal olfactometry the most accurate and reproducible results result from the equalization method.

However, even under the optimum conditions defined hereinbefore olfactometric measurements suffer from the following inconveniences:

the equipment is heavy, cumbersome, fragile and difficult to handle;

the accuracy of intensity measurements is limited by a physiological datum, the smallest perceptible intensity difference corresponding to a concentration increase of the order of 50% (or a decrease of the order of 33%.).

Reproducible results are only obtained by repeating the measurements several times on several different people in such a way as to obtain average values excluding inter-individual variations, as well as intra-individual variations. Thus, it is not possible to reliably measure the odorous intensity of a given stimulus for a given person at a given time.

In man and all animals with equal olfactory organs the sensations received by the olfactory mucosa on one side are transmitted to the olfactory bulb on the same side. The two olfactory bulbs are connected by a nervous circuit which establishes a reciprocal inhibition between them. The more one of the bulbs is activated the more it delays the response of the other. This reciprocal inhibition is at a maximum when the two stimuli are completely synchronous to within one millisecond. It creates between the two olfactory bulbs an unstable equilibrium situation, which increases the differences in inverse proportion to their size. Thus, the equality of intensity of the two stimuli can be very accurately evaluated, the system of the two bulbs then behaving in the manner of a high gain zero detector.

It is possible to provide a device which makes it possible to overcome the disadvantages referred to hereinbefore and in particular a device which can be easily operated and which gives accurate reproducible measurements. This is achieved by physiological zero detection by measuring the equality of the odorous intensities of two separate olfactory stimuli simultaneously supplied each to one side of the person's nose.

The following procedure is adopted. By means of an electronic control released by the experimenter two olfactory stimuli, one constituting a standard and the other the stimulus which is to be measured are simultaneously supplied each to one nostril of the same experimenter. The respective intensities of the stimuli are then compared by the strongest perception felt in a nostril. The intensities in each nostril are then equalized by regulating the amplitude of the stimulus to be measured compared with the standard stimulus. The two stimuli must on the one hand be strictly synchronous and on the other must be separately adjustable in amplitude. Moreover, to eliminate distortions which may be caused by an asymmetry of the nasal cavities it is necessary to proceed as for a double weighing operation, thus for example a standard stimulus E and a stimulus X, whose amplitude it is wished to adjust so that its intensity is equal to that of E. Stimulus E is firstly supplied to the right and it is equalized with an accessory stimulus R supplied to the left and which serves as a tare. Without modifying R stimulus X is then supplied to the right and is equalized with R. Thus, E and X have the same odorous intensity.

The equality of the sensations can be evaluated electro-physiologically in the animal and subjectively in man. In the first case signals collected by electrodes carefully positioned in the two olfactory bulbs are used. In the second case the side where the sensation is most pronounced is indicated verbally. The compared intensities are considered to be equal when the sensation is indicated as being "in the middle" or no stronger "on one side than the other".

A differential olfactometer permitting the performance of supraliminal olfactometric measurements is known and which comprises:

two odour injectors with atomizers mounted on a nasal centering support;

a retractable antidiffusion device which hides the atomizers between stimulation periods;

an electronic control unit and a breathing detection device for controlling the atomizers.

Each injector has an atomizer which is mounted on a reservoir deformable under the action of an elastic transmission controlled by a motor.

Such a differential olfactometer makes it possible to perform supraliminal olfactometric measurements, but has the disadvantage of a pulsed control of the supply to the atomizers from a deformable reservoir and which is required to act synchronously with a retraction control of the antidiffusion device. Moreover the control of the antidiffusion device is realised via the breathing detection device comprising a single sensor positioned in proximity to one of the atomizers. Thus, in the case of pronounced assymmetry in the inhaling power of the nostrils of the experimenter the injection of the olfactory stimuli is not initiated at the most appropriate time for the measurements to be performed.

BRIEF SUMMARY OF THE INVENTION

The object of the invention is to obviate these disadvantages and in particular provide a differential olfactometer in which the stimulus reaches the person dynamically and in which the injection of the olfactory stimuli is commenced at the most appropriate time for the olfactometric measurements.

The invention relates to a differential olfactometer comprising two atomizers located on either side of a nasal support and respectively associated with a circuit for supplying olfactory stimuli, a retractable antidiffusion device which hides the atomizers during the intervals between nasal stimulation periods and a breathing detection device associated with an electronic control unit for controlling the hiding of the atomizers, wherein the supply circuit for the atomizers comprises means for permanently supplying the latter.

According to an advantageous feature of the invention the breathing detection device comprises two temperature sensors located in the vicinity of in each case one atomizer and associated with the electronic control unit for hiding the atomizers and a coincidence detector connected to the two sensors and to the electronic control unit controlling the retraction of the antidiffusion device when the sensors are simultaneously cooled.

According to a special feature of the invention each of the atomizers comprises a pipe with a calibrated opening.

According to a further feature of the invention the antiduffusion device comprises for each atomizer a sheath surrounding the pipe having in its upper part on the side of the pipe opening an opening which permits the passage of said pipe, whilst its lower part which is wider than the pipe issues into a permanent pumping chamber, said sheath being associated with the electronic control unit by means for displacing it in a linear manner along the pipe in such a way that the pipe is entirely contained within the sheath when the coincidence detector does not supply a control signal and wherein the pipe emerges from the sheath opening when the coincidence detector supplies a retraction control signal.

BRIEF DESCRIPTION OF THE DRAWINGS

Other features and advantages of the invention can be gathered from the following detailed description of non-limitative embodiments and with reference to the attached drawings, wherein show.

DETAILED DESCRIPTION OF THE PREFERRED EMBODIMENTS

Figure 1:
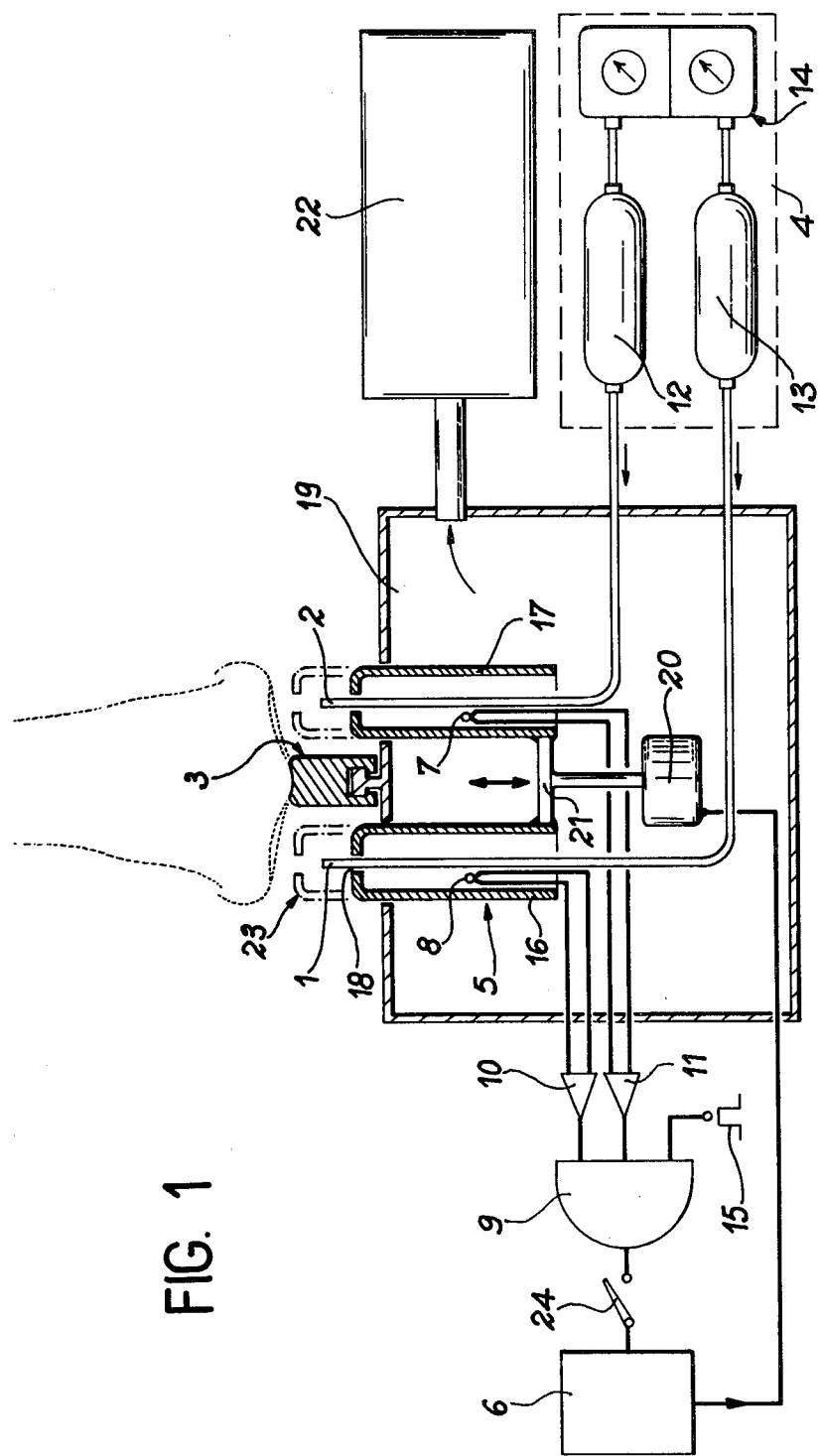
FIG. 1 an olfactometer according to the first embodiment of the invention.

FIG. 1 shows a first embodiment of an olfactometer according to the invention which comprises two atomizers 1, 2 located on either side of a nasal support 3. These atomizers are associated with a circuit 4 for supplying olfactory stimuli. A retractable antidiffusion device 5 is associated with the atomizers in such a way that the latter are hidden during the intervals between the nasal stimulation periods. An electronic control unit 6 associated with a breathing detection device makes is possible to control the hiding of the atomizers. This electronic control unit comprises temperature sensors 7, 8 acting on a coincidence detector 9 via amplifiers 10, 11. The supply circuit 4 for the atomizers comprises means for permanently supplying the latter. These means comprise odour cartridges 12, 13, each of which contains an odorous product or an odorous mixture. Cartridge 12 can for example be that chosen for reference purposes. Each of the cartridges issues respectively into an atomizer and means 14 for supply by a gaseous fluid with a regulatable pressure. This gaseous fluid is for example pressurized nitrogen or air. The cartridges can be made from glass or metal and the odorous product or odorous mixture is generally contained in a porous body located within the cartridges. The flow rate of the olfactory stimuli is regulated on the one hand by the pressure of the gaseous fluids supplied by means 14 and on the other hand as a result of the size of the opening of atomizers 1, 2. One of the temperature sensors 7, 8 is located in the vicinity of each atomizer and the coincidence detector 9 supplies the electronic control unit 6 with a signal controlling the retraction of antidiffusion device 5, when said sensors undergo simultaneous cooling. This simultaneous cooling occurs when the experimenter, whose nose rests on the nasal support 3 inhales above the atomizers. The simultaneity of this cooling is brought about by coincidence detector 9 which is a logic gate of the AND type with two inputs, whereby each input remains active for a few milliseconds and when the two inputs are simultaneously active a signal is transmitted to the electronic control unit 6 which supplies the signal for controlling the retraction of the antidiffusion device 5.

For each of the atomizers antiduffusion device 5 has sheaths 16, 17 which embrace the pipes formed by the atomizers. In the upper part of each sheath there is an opening 18 permitting the passage of the pipe. The lower part of each sheath is wider than the pipe and issues into a permanent pumping chamber 19. The antidiffusion device 5 also has means permitting the linear displacement of the sheaths along the pipes of injectors 1, 2 in such a way that the pipe is entirely contained within the sheath when the coincidence detector supplies no control signal. The pipe emerges from the sheath opening when the coincidence detector supplies a retraction control signal. In this first embodiment of the olfactometer according to the invention the means permitting the displacement of the sheaths comprise an electromagnetic motor 20 with alternating linear displacements. This known motor is not shown in detail in the drawing and is associated with a member 21 for connecting the sheaths and is controlled by electronic control unit 6. Pumping chamber 19 is obviously connected to a pump 22 permitting permanent pumping in the volume of the sheaths in such a way as to prevent any propagation of the stimulus when the sheaths are in the upper position.

The olfactometer then functions in the following manner. With the reference stimulus for example in cartridge 12 and the odorous gas to be tested in cartridge 13 the experimenter places his nose on nasal support 3 and closes the switch 24 making it possible to connect the output of coincidence detector 9 to the input of electronic control unit 6. Sheaths 16, 17 are initially in the upper position 23. As soon as the experimenter inhales sensors 7 and 8 are cooled and if this cooling occurs virtually simultaneously to within for example 5 milliseconds the AND gate 9 is conductive and a retraction control signal of sheaths 16, 17 of the antidiffusion device reaches electronic control unit 6. As will be shown hereinafter this electronic control unit 6 has means making it possible to fix a regulatable time lag for applying a retraction control signal to motor 20. Unit 6 also has means for fixing a retraction period for the sheaths from the end of said time lag. For example the time lag introduced into the retraction of the sheaths is approximately 100 milliseconds, whilst the retraction period is 50 milliseconds. As will be shown in greater detail hereinafter said time lag and said period make it possible to perform an olfactometric measurement at the time when the olfactory sensitivity of the experimenter is at a maximum. When the sheaths are retracted in this way the reference stimulus and the odorous gas to be tested respectively reach each of the nostrils of the experimenter. It is then sufficient to regulate the pressure of the odourless gas injected into test cartridge 13 until an equivalent odour intensity sensation is obtained in each of the nostrils. The experimenter can then reverse the test and reference cartridges and recommence the same operation. The odour intensity perceived by the experimenter in each of his nostrils can then be expressed as a function of the odourless gas pressure supplied by means 14 supplying each of the cartridges with odourless gas. As has been shown hereinbefore the experimenter can also effect an olfactometric measurement by using the double weighing method. When sheaths 16, 17 are in the upper position the pumping means 22 evacuate the olfactory stimuli above atomizers 1, 2, in such a way that the experimenter does not perceive these stimuli.

Figure 2:
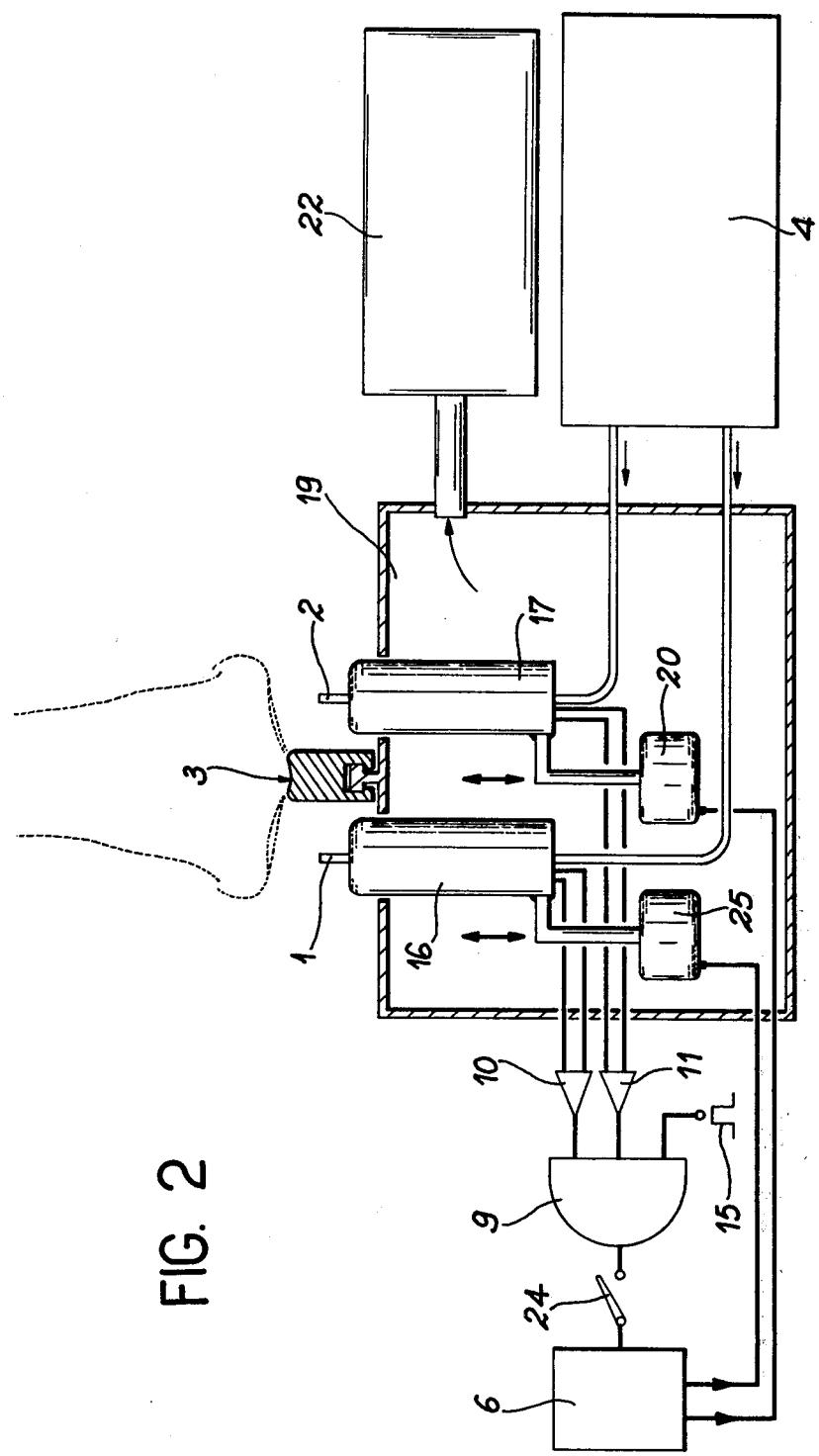
FIG. 2 an olfactometer according to a second embodiment of the invention.

FIG. 2 shows another embodiment of the olfactometer according to the invention. The same members carry the same reference numerals in FIGS. 1 and 2. According to this second embodiment of the olfactometer according to the invention the means permitting the linear displacement of the sheaths along atomizers 1, 2 comprise in the case of each of the atomizers an electromagnetic motor with alternating linear displacements. These motors are shown at 20 and 25. As hereinbefore each of the motors receives a control signal from the electronic control unit 6. The control signal received by each of the motors is obviously applied with a time lag and persists for a predetermined time. The olfactometric measuring principle is the same as that used in the first embodiment. The differences between these two embodiments are essentially based on the presence of two motors 20, 25, permitting a separate control of the retraction of the sheaths. There is also a difference with respect to the electronic control unit 6 which will be described in greater detail hereinafter.

Figure 3:
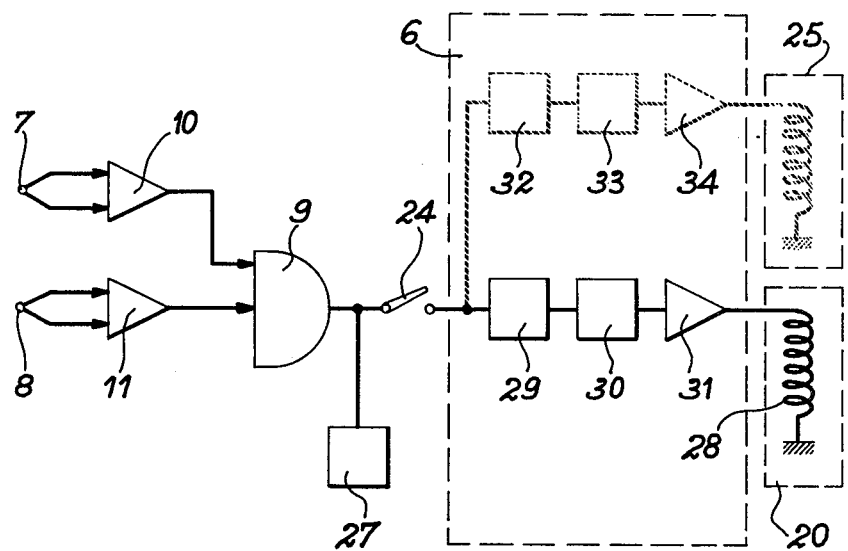
FIG. 3 the breathing detection device associated with the electronic control unit permitting the control of the hiding of the atomizers.

FIG. 3 shows the electronic control unit 6 associated with the coincidence detector 9 constituted by an AND gate which permits the detection of the simultaneity of the cooling of thermal sensors 7 and 8, whose output signals act on the inputs of said gate via amplifiers 10, 11. When a simultaneous cooling of thermal sensors 7, 8 is detected a control signal is transmitted to electronic control unit 6. The experimenter is made aware of this cooling by a visual or sound indicator 27. Obviously an olfactometric measurement can only be performed on closing switch 24. In the first embodiment of the olfactometer according to the invention described with reference to FIG. 1 the control signal brings about the retraction of sheaths 16, and 17 due to the linear displacement motor 20. This motor can be similar to those used in loud-speakers. The drawing merely shows a coil 28 which moves in a magnetized yoke. This coil controls the alternating linear displacement of sheaths 16, 17. In the first embodiment of the invention the electronic control unit has means 29 which makes it possible to delay the control signal and means 30 permitting the fixing of a period for applying the control signal to motor 20. Means 29 permitting the fixing of a delay for the application of the control signal comprise a monostable flip-flop, whose cycle can be fixed for example at 100 milliseconds. Means 30 permitting the fixing of a control signal application period also comprise a monostable flip-flop having for example a 50 millisecond cycle. Monostable flip-flop 30 is associated with an amplifier 31, whose output controls coil 28 of motor 20. In the second embodiment of the olfactometer of the invention the retraction of sheaths 16, 17 is controlled separately by motors 20 and 25. As a result the electronic control unit has a second control line which, as hereinbefore, comprises means for fixing a time lag and an application period for the control signal to another motor 25. As hereinbefore these means comprise a monostable flip-flop 32 which fixes the delay in the application of the control signal and a monostable flip-flop 33 fixing the application period of said signal to motor 25 via an amplifier 34. In principle the time lags and application times on the two control lines 20 and 25 are identical, but obviously they can be regulated as a function of the measurements and studies which the experimenter wishes to perform.

Figure 4:
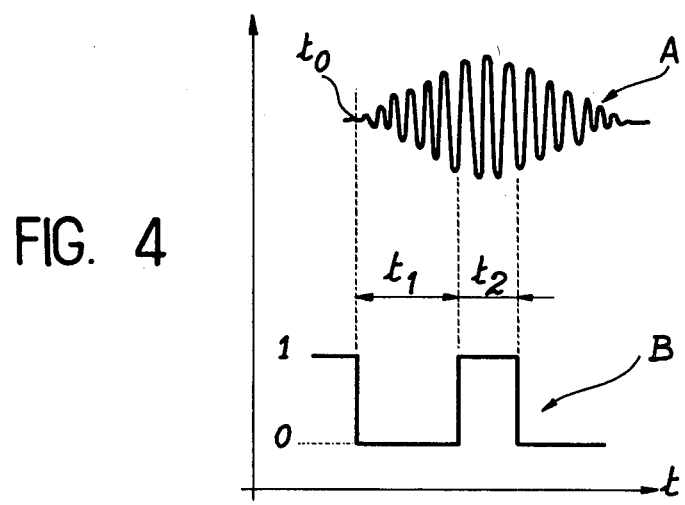
FIG. 4 a diagram showing the signals appearing at certain points of the control unit of FIG. 3.

FIG. 4 shows as a function of time t the diagram A showing the development of the amplitude of an inhalation. At B are shown the signals obtained at the output of the monostable flip-flops 29 and 30 of FIG. 3. At the time of an inhalation the control signal transmitted by AND gate 9 reaches monostable flip-flop 29 at time $t_0$, thereby fixing the delay in applying the control signal to motor 20. This delay or time lag $t_1$ can for example be 100 milliseconds. It makes it possible to apply the sheath retraction control signal at the time when the inhalation represented on diagram A has a maximum amplitude. The end of the cycle of the monostable flip-flop 29 corresponds to the actuation of the monostable flip-flop 30 permitting the fixing of the application time $t_2$ of the control signal to motor 20. This period can for example be 50 milliseconds. It permits a retraction of the sheaths for a time corresponding to a maximum inhalation amplitude.

Figure 5:
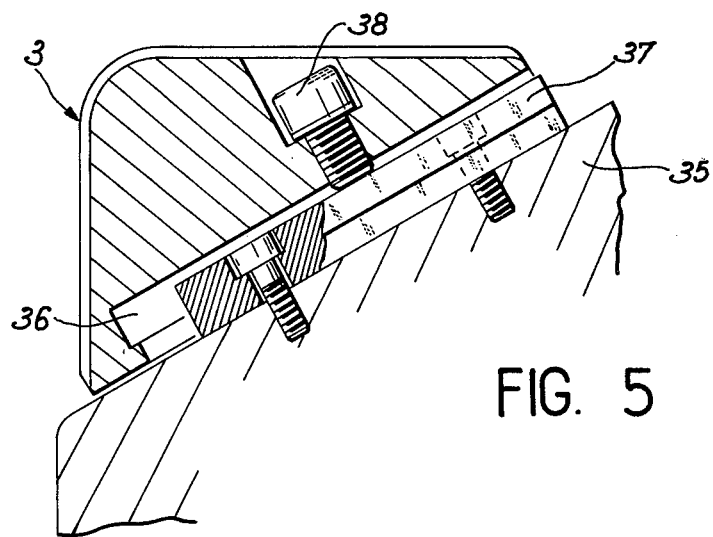
FIG. 5 a lateral section of the nasal support whose position is regulatable.

FIG. 5 shows the nasal support of FIG. 1 in cross-section. It is positioned on an inclined base 35 of the olfactometer. A T-shaped channel 36 slides along a T-shaped strip 37. The support 3 is maintained on the strip by means for example of screws 38. This displacement of support 3 on the inclined plane of base 35 permits the positioning of the height of the experimenter's nose relative to the openings of atomizers 16 and 17.

Figure 6:
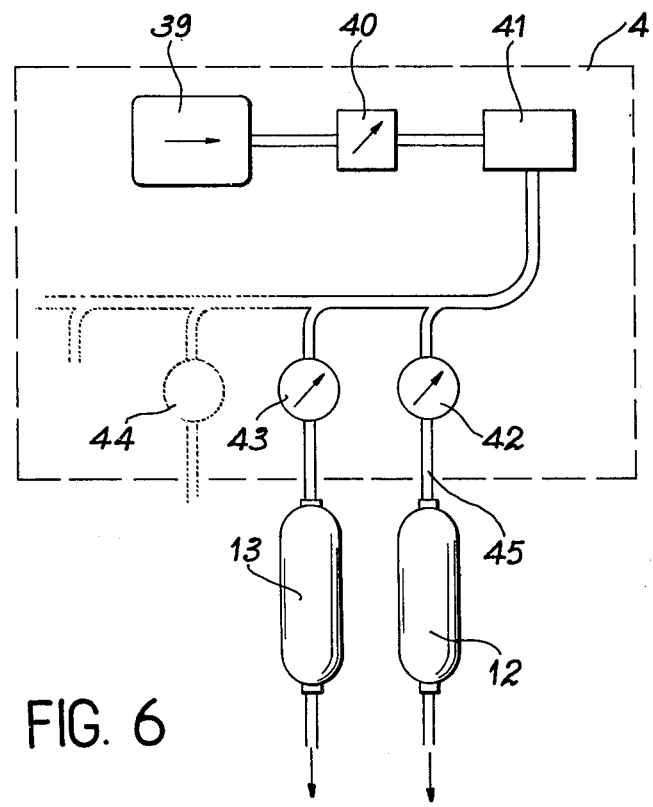
FIG. 6 in part a supply circuit which can be associated with several olfactometers.

FIG. 6 shows part of the supply circuit 4 which can be associated with a plurality of olfactometers. The supply circuit has a pressurized odourless gas or compressed air source 39 associated with a pressure regulator 40. The outlet of the regulator supplies a deodourizing activated carbon filter 41. At the filter outlet it is possible to connect odour cartridges 12, 13, etc. supplying a plurality of olfactometers. The pressure of the compressed air or the odourless gas in the cartridges can be regulated by means of pressure gauges 42, 43, 44, etc. The tubes such as 45 connecting the pressure gauge to the cartridges may also be used for regulating the flow of gaseous fluid injected into these cartridges. For this purpose it is merely necessary to select the length or cross-section of the tubes as a function of the desired flow rate.

The olfactometer described hereinbefore makes it possible to perform reliable and rapid odour intensity measurements on the basis of a synchronous evaluation. The reference stimulus and the odorous gas to be tested are released simultaneously into the two nostrils. As a result of this olfactometer the greatest advantage is drawn from a contrast amplification between the two olfactory bulbs. Thus, the bulbs have a reciprocal inhibiting action on one another and obliterate the stimulation which is stimulated least. In the case of an intensity difference of 5 to 10% there is a subjective sensation of unilateral stimulation. This contrast effect is not influenced by qualitative differences between the odorous flows sampled in each nostril. The contrast is maximum when the two stimuli are supplied with a time lag below one millisecond. The olfactometer according to the invention makes it possible to obtain this simultaneity in the injection of the two olfactory stimuli. The thermal detectors are heated at the time when the experimenter exhales and suddenly cool when he inhales. The control signal supplied by the coincidence detector is sensitive to the simultaneous cooling of the two thermal sensors and brings about a simultaneous retraction of the two sheaths surrounding the atomizers. The heat signals from the thermal sensors are separately amplified and their time lag is compared with a very small tolerance of a few milliseconds in the detector constituted by the AND gate. Thus, for each smell there is a true measurement of the two nostrils of the person concerned.

Thus, any vascular evolution of the nasal cavity is prevented and the only measurements which are taken into account are those corresponding to completely bilateral, synchronous smelling operations.

The invention is not limited to the embodiments described and represented hereinbefore and various modifications can be made thereto without passing beyond the scope of the invention.

What is claimed is:

1. A differential olfactometer comprising two atomizers located on either side of a nasal support and respectively associated with a circuit for supplying olfactory stimuli, a retractable antidiffusion device which hides the atomizers during the intervals between nasal stimulation periods and a breathing detection device associated with an electronic control unit for controlling the hiding of the atomizers, wherein the supply circuit for the atomizers comprises means for continuously supplying the olfactory stimuli to the atomizers in a continuous stream during the entire time period of inhalation.

2. An olfactometer according to claim 1, wherein the breathing detection device comprises two temperature sensors located in the vicinity of in each case one atomizer and associated with the electronic control unit for hiding the atomizers and a coincidence detector connected to the two sensors and to the electronic control unit controlling the retraction of the antidiffusion device when the sensors are simultaneously cooled.

3. An olfactometer according to claim 2, wherein each of the atomizers comprises a pipe with a calibrated opening.

4. An olfactometer according to claim 3, wherein the antidiffusion device comprises for each atomizer a sheath surrounding the pipe having in its upper part on the side of the pipe opening an opening which permits the passage of said pipe, whilst its lower part which is wider than the pipe issues into a permanent pumping chamber, said sheath being associated with the electronic control unit by means for displacing it in a linear manner along the pipe in such a way that the pipe is entirely contained within the sheath when the coincidence detector does not supply a control signal and wherein the pipe emerges from the sheath opening when the coincidence detector supplies a retraction control signal.

5. An olfactometer according to claim 4, wherein the means for diplacing the sheaths comprise an electromagnetic motor with alternating linear displacements, associated with a member for connecting the sheaths, said motor being controlled by the electronic control unit.

6. An olfactometer according to claim 5, wherein the electronic control unit has means for fixing a regulatable time lag in the application of the retraction control signal to the motor and means for fixing a retraction period starting from the end of said time lag.

7. An olfactometer according to claim 4, wherein the means for displacing the sheaths comprise for each sheath an electromagnetic motor with alternating linear displacements controlled by the electronic control unit.

8. An olfactometer according to claim 6, wherein the electronic control unit has for each of the motors means for fixing a regulatable time lag in the application of the retraction control signal to the motor and means for fixing a retraction period starting from the end of this time lag.

9. An olfactometer according to claim 8, wherein the means for fixing the time lag and the duration of retraction comprise monostable flip-flops with regulatable cycle times.

10. An olfactometer according to claim 3, wherein the circuit for supplying the atomizers with olfactory stimuli has for each of the atomizers a cartridge containing an odorous product, said cartridge issuing on the one hand onto the atomizer and on the other hand onto means for supplying the cartridge with a gaseous fluid whose pressure can be regulated.

11. An olfactometer according to claim 2, wherein the temperature sensors are thermocouples, which are respectively connected to the coincidence detector via an amplifier.

12. An olfactometer according to claim 10, wherein the coincidence detector is a logic AND gate, each of whose inputs receives a signal of regulatable duration.

13. An olfactometer according to claim 12, wherein a switch is connected between the output of the AND gate and the input of the electronic control unit for the olfactometric measurements.

14. A differential olfactometer according to claim 2, wherein the odorous products or odorous mixtures are supplied to the atomizers by two separate lines.

15. A differential olfactometer according to claim 2, further comprising means for regulating the position of the nasal support relative to the atomizers.

* * * * *